(12) United States Patent
Ishigaki et al.

(10) Patent No.: US 7,153,837 B2
(45) Date of Patent: Dec. 26, 2006

(54) AGENT FOR PROTECTION OF RETINAL NEURONS

(75) Inventors: Kaoru Ishigaki, Kanagawa (JP); Hiroshi Kojima, Saitama (JP); Shigehisa Okaguchi, Tokyo (JP); Shinji Yoneda, Nara (JP); Hideaki Hara, Nara (JP); Nobuaki Miyawaki, Hyogo (JP)

(73) Assignee: Ortho-McNeil Pharmaceutical Inc., Raritan, NJ (US)

( * ) Notice: Subject to any disclaimer, the term of this patent is extended or adjusted under 35 U.S.C. 154(b) by 207 days.

(21) Appl. No.: 10/481,473

(22) PCT Filed: Jun. 14, 2002

(86) PCT No.: PCT/JP02/05935

§ 371 (c)(1),
(2), (4) Date: Dec. 17, 2003

(87) PCT Pub. No.: WO02/102369

PCT Pub. Date: Dec. 27, 2002

(65) Prior Publication Data
US 2004/0171558 A1    Sep. 2, 2004

(30) Foreign Application Priority Data
Jun. 18, 2001  (JP)  ............... 2001-183192

(51) Int. Cl.
*A01N 43/04*   (2006.01)
*A01N 43/16*   (2006.01)
*A61K 31/70*   (2006.01)

(52) U.S. Cl. .................. 514/23; 514/454; 514/459

(58) Field of Classification Search .......... 514/23, 514/454, 459
See application file for complete search history.

(56) References Cited

U.S. PATENT DOCUMENTS
4,513,006 A    4/1985    Maryanoff et al.

FOREIGN PATENT DOCUMENTS
JP         5-5824 B2        4/1985
WO      WO 98/00124 A1     1/1998
WO      WO 00 61138 A     10/2000

OTHER PUBLICATIONS

Abstract of Graefe's Arch. Clin. Exp. Ophthalmol., (1996), 234(7), 445-451.
Abstract of Graefe's Arch. Clin. Exp. Ophthalmol., (1996), 234(Suppl. 1), S209-S213.
Abstract of Journal of Ocular Pharmacology and Therapeutics, (1995), 11(3), 253-259.
Chang, C., et al, "Apoptotic photoreceptor cell death after traumatic retinal detachment in humans" Abstract of Archives of Ophthalmology, (1995), 113(7), 880-886.
Garcia-Venezuela, E., et al, "Programmed cell death of retinal ganglion cells during experimental glaucoma" Experimental Eye Research, (1995), 61(1), 33-44.
Johns, Donald R., et al, "Treatment of Leber's hereditary optic neuropathy: theory to practice" Seminars in Ophthalmology, (2002), 17(1), 33-38.
Markind, J.F., "Topiramate: A new antiepileptic drug" American Journal of Health-System Pharmacy, (1998), 55(6), 554-562.
Naash, M.L., et al, "Light-induced acceleration of photoreceptor degeneration in transgenic mice expressing mutant rhodopsin" Investigative Ophthalmology and Visual Science, (1996), 37(5), 775-782.
Nakamura, J., et al, "Target pharmacology of topiramate, a new antiepileptic drug" Abstract of Journal of Japanese Pharmacology, (2000), 115, 53-57.
Portera-Cailliau, C., et al, "Apoptotic photoreceptor cell death in mouse models of retinitis pigmentosa" Proc. Natl. Acad. Sci, USA, (1994), 91, 974-978.
Quigley, H.A., et al, "Retinal ganglion cell death in experimental glaucoma and after axotomy occurs in apoptosis" Investigative Ophthalmology and Visual Science, (1995), 36(5), 774-786.
Tso, M.O.M., et al., "Apoptosis leads to photoreceptor degeneration in inherited retinal dystrophy of RCS rats" Investigative Ophthalmology and Visual Science, (1994), 35(6), 2693-2699.
PCT International Search Report dated Nov. 29, 2002, for PCT Intl. Appln. No. PCT/JP02/05935.

*Primary Examiner*—James O. Wilson
*Assistant Examiner*—Traviss C. McIntosh, III
(74) *Attorney, Agent, or Firm*—Mary Appollina

(57) ABSTRACT

This invention relates to an agent for the protection of retinal neurons which comprises, as an effective ingredient, sulfamate derivative having the following formula:

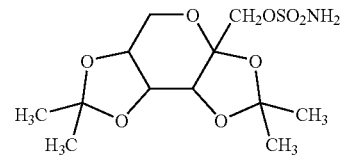

and to a method for the protection of retinal neurons by using said sulfamate derivative.

11 Claims, No Drawings

AGENT FOR PROTECTION OF RETINAL NEURONS

This application is a National Stage application under 35 U.S.C. 371 of Application No. PCT/JP02/05935 filed Jun. 14, 2002, which claims priority from JP 2001-183192, filed Jun. 18, 2001.

1. Technical Field

This invention relates to an agent for the protection of retinal neurons which comprises, as an effective ingredient, sulfamate derivative having the following formula:

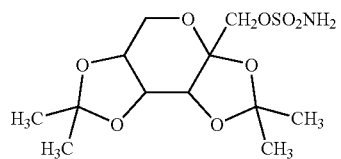

which is represented by topiramate, and to a method for the protection of retinal neurons by using said sulfamate derivative.

2. Background Art

Retina has a function to receive light from outside, and plays an important role for visual function. Retina is structurally a tissue having a thickness of about 0.1 to 0.5 mm which is composed of 10 layers such as retinal pigmented layer, inner plexiform layer, ganglion cell layer, nerve fiber layer, etc. In inner plexiform layer, there exist neurons called amacrine cells which are paired with neurite of ganglion cell to form synapse. Since amacrine cells respond well both at the start and at the end of light irradiation, they are considered to work as a detector of light intensity. In ganglion cell layer, there exist neurons whose somas are present on the innermost of retina, and which are deeply involved with motor vision, peripheral vision, color vision and stereoscopic vision. In nerve fiber layer, there run retinal blood vessels which are branches of central artery and vein of retina, and which play a role of supplying optic nerve with oxygen and nourishment.

In glaucoma, disorder in retinal blood circulation or in axonal transport in optic nerve ultimately causes the death of ganglion cell, which in turn is a cause of the defluxion of nerve fiber, which progresses to the loss of visual filed. Hence, there has now been being established so-called "Neuroprotection", i.e., an idea that treatment to prevent or minimize the death of ganglion cell will contribute to ultimate therapy of glaucoma (Ophthalmology, 40, 251–273, 1998). In fact, it has been reported that, in rat with ocular hypertensive-induced ischemia, disorder was observed in retinal ganglion cell layer and in optic nerve head (Graefes Arch. Clin. Exp. Ophthalmol., 234, 445–451, 1996). It has also been reported that, in methylcellulose-induced ocular hypertensive rabbit, there were observed significant decrease in the density of retinal ganglion cells (hereinafter abbreviated as RGCs) and significant increase in glial cells, and that interrelation was perceived to exist between the defluxion of ganglion cell and the size of cells (Graefes Arch. Clin. Exp. Ophthalmol., 234, S209–S213, 1996).

When retinal blood vessels are occluded or narrowed on account of twitching, thrombus or arteriosclerosis, disorder occurs in retinal blood circulation, and, thus, the supply of oxygen and nourishment to retina or optic nerve is shut off. The disorder of retinal blood circulation occupies especially an important position in retinal diseases. Examples of representative symptoms which are accompanied by the disorder of retinal blood circulation include retinal embolism wherein retinal vein or retinal artery is occluded or narrowed, diabetic retinopathy which is a cause of retinodialysis, and ischemic optic neuropathy wherein the loss of visual function occurs. This disorder of retinal blood circulation further causes insufficient supply of oxygen or nourishment, which leads to the death of RGCs. Also in other retinal diseases such as macular degeneration, retinitis pigmentosa and Leber's disease, it is considered that this death of ganglion cell is deeply involved in the occurrence of disease.

Furthermore, it is now being clarified that apoptosis, which is a form of programmed death of cell, takes part in various aspects of ocular disorder. It has been reported that apoptosis occurs in RGCs in the case of, for instance, retinal disorder caused by ischemia-reperfusion (J. Ocul. Pharmacol. Ther., 11, 253–259, 1995), retinodialysis (Arc. Ophthalmol., 113, 880–886, 1995), retinitis pigmentosa (Proc. Natl. Acad. Sci. USA, 91, 974–978, 1994; Invest. Ophthalmol. Vis. Sci., 35, 2693–2699, 1994), light induced retinal disorder (Invest. Ophthalmol. Vis. Sci., 37, 775–782, 1996) and glaucoma (Invest. Ophthalmol. Vis. Sci., 36, 774–786, 1995; Exp. Eye Res., 61, 33–44, 1995). Thus, it is highly possible that, although various causes are concerned, the apoptosis of neurons which constitute visual information network is directly involved in the resultant loss of visual function.

Topiramate, on the other hand, is known [e.g., Japanese Patent Publication KOKOKU No. Hei 5 (1993)-5824] to be a compound having anticonvulsion activity, and to have the following formula:

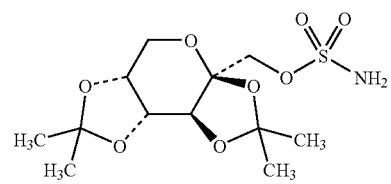

2,3:4,5-bis-O-(1-methylethylidene)-β-D-fructopyranose sulfamate, and, it has been reported (Journal of Japanese Pharmacology, 115, 53–57, 2000; Am, J, Health-Syst Pharm, 55, 554–562, 1998) that topiramate is effective as an antiepileptic agent. Topiramate has also an action to inhibit carbonic anhydrase which takes part in the production of aqueous humor, and has been reported [e.g., Japanese Patent Publication KOKOKU No. Hei 5 (1993)-5824] to be useful, as an ocular hypotensive agent, for the therapy of glaucoma.

PCT WO 00/61138 discloses that topiramate and its derivatives are useful for the treatment of chronic neurodegenerative disorder including diabetic neuropathy and diabetic retinopathy.

Furthermore, PCT WO 98/00124 discloses that topiramate and its derivatives are useful for the treatment of acute ischemic neuropathy.

There has, however, been no report about the influence of topiramate on retinal diseases in which carbonic anhydrase does not participate, such as retinal embolism, ischemic optic neuropathy, macular degeneration, retinitis pigmentosa or Leber's disease, and on ocular diseases such as glaucomatous neuropathy. Nor has anything been known as to the influence of topiramate on ocular tissues, in particular on retinal neurons such as RGCs.

DISCLOSURE OF INVENTION

During the process of research and development of topiramate as an agent for the therapy of glaucoma, the inventors of the present invention have unexpectedly found out that a sulfamate derivative of the foregoing formula (I) which is represented by topiramate acts directly on retinal neurons to effectively protect retinal neuron from apoptosis, and that topiramate has also an excellent effect to prevent both the decrease of cells in ganglion cell layer and the thinning of inner plexiform layer, and further that topiramate is therefore useful for the prophylaxis or therapy of various diseases caused by the apoptosis of retinal neuron, such as glaucomatous neuropathy, or of retinal diseases such as retinal embolism, ischemic optic neuropathy, macular degeneration, retinitis pigmentosa or Leber's disease, and, thus, the inventors have completed the present invention.

The present invention provides an agent for the protection of retinal neurons which is characterized by comprising, as an effective ingredient, sulfamate derivative which has the following formula:

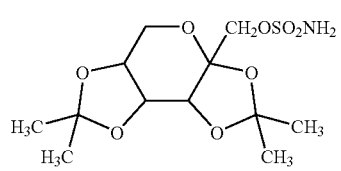   (I)

The present invention, furthermore, provides a method for the protection of retinal neurons of a subject, which is characterized by administering the sulfamate derivative of the above formula (I) to the subject.

Sulfamate derivative of formula (I) has optical isomer and diastereomer. The sulfamate derivative of formula (I) which is used as an effective ingredient for the agent of the present invention includes these isomers and a mixture thereof. The sulfamate derivative of formula (I) which is used in the present invention may take the form of hydrate for instance. Among the sulfamate derivatives of formula (I), topiramate of the foregoing formula (II) is in particular preferable.

Retinal neurons which are to be protected by the agent of the present invention include RGCs, amacrine cells, bipolar cells, horizontal cells and photoreceptor cells. The agent of the present invention has an effective action especially on the apoptosis of RGCs among the above-mentioned retinal neurons.

The following pharmacological tests with use of topiramate give details of the action of the sulfamate derivative of formula (I) of the present invention to protect retinal neurons:

[Pharmacological Tests]

In order to study its action to protect retinal neurons, topiramate was tested, by the following method, for (1) action on the glutamate-induced death of cultured retinal neurons of rat fetus, and for (2) action on ischemia-induced retinal damage of rat.

(1) Topiramate's Action on the Glutamate-Induced Death of Cultured Retinal Neurons of Rat Fetus:

From rat fetuses (aged 17 to 19 days), retinal cells were taken out and isolated, and were cultured on a polyethyleneimine-coated plastic-covered slip in a 10% bovine fetal serum-containing Eagle's basal medium for seven days. From the eighth day, they were cultured in a 10% equine serum-containing Eagle's basal medium. On the sixth day of culture, cytosine arabinoside (10 μM) was added to inhibit the proliferation of non-neuronal cells. Next, the cells were incubated (37° C., 5% $CO_2$.95% air) for 10 minutes in a medium which had been prepared by adding glutamate (1 mM) and topiramate in various concentrations (10 nM~100 μM) to serum-free Eagle's basal medium. Then, cells were returned to serum-free Eagle's basal medium which contained neither glutamate nor topiramate, and were incubated (37° C., 5% $CO_2$.95% air) for one hour, and, thereafter, toxicity was determined by trypan blue exclusion method. In detail, cells were immobilized with 10% neutral formalin solution, and were washed with physiological saline. Then, cells were dyed by adding trypan blue solution, and, thus, the number of cells was counted by phase-contrast microscope. Cells which had been dyed with trypan blue were regarded as dead, and non-dyed cells as surviving, and, thus, the survival rate of cultured cells was found from the proportion of the number of surviving cells to the number of total cells counted (at least 200). The group to which 1 mM of glutamate had been added and the group to which both 1 mM of glutamate and topiramate in various concentrations had been added are respectively called "Single 1 mM glutamate added group" and "1 mM glutamate+topiramate (various concentrations) added group". Results concerning these groups were compared with the corresponding measured values of "Untreated group", i.e., a group which had received no treatments. Results are shown in Table 1. The values in the table are average values.

TABLE 1

| Agent* | Survival rate of cultured retinal neurons (%) |
|---|---|
| Untreated group (7) | 67 |
| Single 1 mM glutamate added group (8) | 46 |
| 1 mM glutamate + 10 nM topiramate added group (7) | 50 |
| 1 mM glutamate + 100 nM topiramate added group (7) | 58 |
| 1 mM glutamate + 1 μM topiramate added group (7) | 60 |
| 1 mM glutamate + 10 μM topiramate added group (8) | 64 |
| 1 mM glutamate + 100 μM topiramate added group (7) | 65 |

*Figure in parentheses shows the number of samples in each group.

(2) Topiramate's Action on Ischemia-Induced Retinal Damage in Rat:

Anesthesia was indued in rat with 3% halothane, and, then, anesthesia was maintained with 1% halothane (halothane was vaporized with 0.5 l oxygen/min. and 1.5 l dinitrogen monoxider/min.). Next, mydriasis was caused in right eye with atropine, and, then, 30 G injection needle which was connected with a vessel of physiological saline for instillation via a tube hung from the ceiling was stuck into anterior chamber, and, thus, a 130 mmHg hydraulic pressure was given, and ischemia was thereby induced After 45 minutes, the injection needle was removed, and retinal blood flow was allowed to make reperfusion. Administration was conducted by intraperitoneal injection into rats with physiological saline (solvent) and topiramate (200 mg/kg body weight) dissolved (partially suspended) in solvent, respectively. The administration was carried out twice respectively, i.e., two hours before and immediately after inschemia. Seven days after the administration, eyeball was taken out, immobilized overnight in 2% paraformaldehyde- 2.5% glutaraldehyde, subjected to paraffin embedding, and was sectioned, and, thus, retinal slices (with a thickness of 3 μm) stained with hematoxylin-eosin (HE) were prepared. From eight slices which had been cut with an interval of 60 μm per one eyeball so that optic nerve head might be covered, three slices were optionally selected. With regard to thus selected three slices, there was taken a photograph of retina in the range of 1 to 1.5 mm on the left or right side from optic nerve head, and, thus, the number of cells in ganglion cell layer (GCL) in retina and the thickness of inner plaxiform layer (IPL) were measured. The group to which solvent had been administered and ischemia had been induced and the group to which topiramate dissolved in solvent had been administered and ischemia had been induced are respectively called "Solvent-administered group" and "Topiramate-administered group". Results concerning these groups were compared with the corresponding measurements of "Normal (Untreated) group", i.e., a group which had received no such treatments. Results are shown in Table 2. The values in the table are average values.

TABLE 2

| Agent* | Number of cells in GCL (number/mm) | Thickness of IPL (μm) |
| --- | --- | --- |
| Normal (Untreated) group (10) | 68 | 49 |
| Solvent-administered group (10) | 36 | 21 |
| Topiramate-administered group (10) (Dose: 200 mg/kg) | 44 | 30 |

*Figure in parentheses shows the number of samples in each group.

It is seen in the results which are shown in Table 1 above that topiramate has an effect to remarkably inhibit the death (apoptosis) of cultured retinal neurons in a concentration-dependent manner. In the results which are shown in Table 2 above, on the other hand, it is seen that topiramate is excellent in effectively preventing both the decrease of number of cells in ganglion cell layer and the thinning of inner plexiform layer.

Hence, sulfamate derivative of the foregoing formula (I) which is represented by topiramate is very useful as an agent to protect retinal neurons such as RGCs, for example as an agent for the prophylaxis or therapy of retinal diseases such as retinal embolism, diabetic retinopathy, ischemic optic neuropathy, macular degeneration, retinitis pigmentosa or Leber's disease, or of ocular diseases such as glaucomatous neuropathy.

When used for the prophylaxis or therapy of these ocular diseases, sulfamate derivative of formula (I) can be administered to a patient (mammal, particular human) either perorally or parenterally, and is formulated into a dosage form suitable for administration together with, as circumstances might demand, pharmaceutically acceptable additives. Examples of dosage form suitable for peroral administration include tablet, capsule, granule and powder. Examples of dosage form suitable for parenteral administration include injection agent, eye drop, nasal drop and suppository. Preparations in these dosage forms can be manufactured by normal technique which has generally been employed in this field.

For instance, tablet can be manufactured by appropriately selecting excipient such as lactose, glucose, D-mannitol, anhydrous calcium hydrogen phosphate, starch and sucrose; disintegrant such as carboxymethylcellulose, calcium carboxymethylcellulose, Croscarmellose Sodium, Crospovidone, starch, partially gelatinized starch and low-substituted hydroxypropylcellulose; binder such as hydroxypropylcellulose, ethylcellulose, gum arabic, starch, partially gelatinized starch, polyvinylpyrrolidone and polyvinylalcohol; lubricant such as magnesium stearate, calcium stearate, talc, hydrous silica and hydrogenated oil; coating agent such as purified sugar, hydroxypropylmethylcellulose, hydroxypropylcellulose, methylcellulose, ethylcellulose and polyvinylpyrrolidone; and corrigent such as citric acid, Aspartame, ascorbic acid and menthol.

Injection agent can be prepared by using sterile purified water and sodium chloride for isotonization.

Eye drop can be manufactured by selecting, as circumstances might demand, from among isotonicity such as sodium chloride and concentrated glycerin; buffer such as sodium phosphate and sodium acetate; surfactant such as polyoxyethylene sorbitan monooleate, polyoxyl 40 stearate and polyoxyethylene hydrogenated castor oil; stabilizer such as sodium citrate and disodium edetate; and antiseptic such as benzalkonium chloride and paraben (phonetic). This eye drop may have any pH value so long as it is within a range which is allowable for ophthalmologic preparation. Preferably, however, the pH is in the range of 4 to 8.

The dose of sulfamate derivative of formula (I), e.g., topiramate, may be varied according to dosage form, the degree of symptom of the patient to which topiramate is to be administered, the age and body weight of the patient and the judgment of doctor. In the case of peroral administration, 0.1 to 2000 mg may be administered to an adult either at one time or separately per day. In the case of injection agent, 0.01 to 200 mg may usually be administered to an adult either at one time or separately per day. In the case of eye drop, a dose having a concentration of effective ingredient of 0.1~10% (w/v) may be administered either once or several times per day.

The following Examples of dosage form give details of the agent of the present invention. The present invention is, however, not restricted by these dosage forms.

FORMULATION EXAMPLES

Example 1 Tablet

| Formulation: | Topiramate | 1 mg |
| --- | --- | --- |
| | Lactose | 66.4 mg |
| | Corn starch | 20 mg |
| | Calcium carboxymethylcellulose | 6 mg |
| | Hydroxypropylcellulose | 6 mg |
| | Magnesium stearate | 0.6 mg |
| | Total: | 100 mg |

Topiramate, lactose and corn starch were mixed in a mixer, and, to the resultant mixture, calcium carboxymethylcellulose and hydroxypropylcellulose were added and granulated. Thus obtained granules were regulated after dried, and, to thus regulated granules, magnesium stearate was added and mixed, and the obtained mixture was compressed by a tablet machine into tablets.

Example 2 Injection Agent

| Formulation: | Topiramate | 10 mg |
|---|---|---|
| | Sodium chloride | 90 mg |
| | Sterile purified water | An amount necessary to make the total 10 ml |

Topiramate and sodium chloride were dissolved in sterile purified water to give an injection agent.

Example 3 Eye Drop

| Formulation: | Topiramate | 1 mg |
|---|---|---|
| | Concentrated glycerin | 250 mg |
| | Polysorbate 80 | 200 mg |
| | Monobasic sodium phosphate 2H$_2$O | 20 mg |
| | 1 N sodium hydroxide | suitable amount |
| | 1 N hydrochloric acid | ″ |
| | Sterile purified water | ″ |
| | Total: | 10 ml |

Topiramate and the other ingredients mentioned above were added to sterile purified water to give an eye drop.

What is claimed is:

1. A method of protecting retinal neurons from apoptosis in an ocular disease in which carbonic anhydrase does not participate selected from the group consisting of glaucomatous neuropathy, retinal embolism, ischemic optic neuropathy, macular degeneration, retinitis pigmentosa, and Leber's disease, comprising administering to a subject in need thereof a therapeutically effective amount of a sulfamate derivative of formula (I):

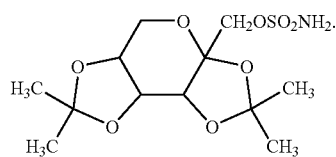

(I)

2. A method as in claim 1 wherein the sulfamate derivative of formula (I) is topiramate.

3. A method as in claim 2 wherein the topiramate is perorally administered in an amount in the range of from about 0.1 to about 2000 mg/day.

4. A method as in claim 2, wherein the topiramate is administered by injection in an amount in the range of from about 0.01 to about 200 mg/day.

5. A method as in claim 2, wherein the topiramate is administered as an eye drop, wherein the concentration of topiramate in the eye drop is in the range of from about 0.1 to about 10% (W/V).

6. A method as in claim 2, wherein the retinal neurons are retinal ganglion cells.

7. A method for the treatment of an ocular disease in which carbonic anhydrase does not participate selected from the group consisting of glaucomatous neuropathy, retinal embolism, ischemic optic neuropathy, macular degeneration, retinitis pigmentosa, and Leber's disease, comprising administering to a subject in need thereof a therapeutically effective amount of a sulfamate derivative of formula (I):

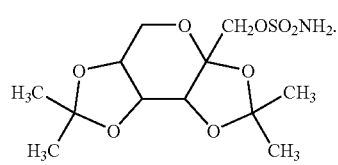

(I)

8. A method as in claim 7, wherein the sulfamate derivative of formula (I) is topiramate.

9. A method as in claim 8, wherein the topiramate is perorally administered in an amount in the range of from about 0.1 to about 2000 mg/day.

10. A method as in claim 8, wherein the topiramate is injected in an amount in the range of from about 0.01 to about 200 mg/day.

11. A method as in claim 8, wherein the topiramate is administered as an eye drop wherein the concentration of topiramate in the eye drop is in the range of from about 0.1 to about 10% (W/V).

\* \* \* \* \*